(12) United States Patent
Brown et al.

(10) Patent No.: US 7,229,994 B2
(45) Date of Patent: Jun. 12, 2007

(54) 4(PHENYL-PIPERAZINYL-METHYL) BENZAMIDE DERIVATIVES AND THEIR USE FOR THE TREATMENT OF PAIN ANXIETY OR GASTROINTESTINAL DISORDERS

(75) Inventors: William Brown, Montreal (CA); Christopher Walpole, Montreal (CA); Niklas Plobeck, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/477,642

(22) PCT Filed: May 16, 2002

(86) PCT No.: PCT/SE02/00956

§ 371 (c)(1),
(2), (4) Date: Nov. 13, 2003

(87) PCT Pub. No.: WO02/094794

PCT Pub. Date: Nov. 28, 2002

(65) Prior Publication Data

US 2004/0147526 A1    Jul. 29, 2004

(30) Foreign Application Priority Data

May 18, 2001  (SE)  .................... 0101772
Nov. 15, 2001 (SE)  .................... 0103820

(51) Int. Cl.
A61K 31/496  (2006.01)
A61K 31/495  (2006.01)

(52) U.S. Cl. ............................ 514/252.13; 514/254.02; 514/254.05; 514/254.1; 514/253.01; 514/255.04; 514/254.04; 544/360; 544/366; 544/369; 544/372; 544/379; 544/396

(58) Field of Classification Search ................ 544/360, 544/369, 379, 366, 370, 372, 396; 514/254.1, 514/252.13, 253.01, 254.05, 255.04, 254.02, 514/254.04

See application file for complete search history.

(56) References Cited

U.S. PATENT DOCUMENTS

| | | | |
|---|---|---|---|
| 3,940,386 A | | 2/1976 | Szabo et al. |
| 5,574,159 A | | 11/1996 | Chang et al. |
| 5,681,830 A | | 10/1997 | Chang et al. |
| 5,807,858 A | | 9/1998 | Chang et al. |
| 5,854,249 A | * | 12/1998 | Chang et al. .......... 514/252.13 |
| 6,130,222 A | | 10/2000 | Roberts et al. |
| 6,680,318 B2 | | 1/2004 | Brown et al. |
| 6,680,321 B1 | | 1/2004 | Roberts et al. |
| 6,696,447 B2 | * | 2/2004 | Brown et al. .......... 514/252.13 |
| 6,784,181 B2 | | 8/2004 | Brown et al. |
| 7,030,124 B2 | * | 4/2006 | Chang et al. .......... 514/255.04 |
| 2006/0142296 A1 | * | 6/2006 | Brown et al. .......... 514/252.13 |

FOREIGN PATENT DOCUMENTS

| | | |
|---|---|---|
| DE | 24 31 178 | 1/1975 |
| DE | 29 00 810 | 7/1980 |
| EP | 0 133 323 | 2/1985 |
| EP | 0 166 302 | 1/1986 |
| EP | 0 283 310 | 9/1988 |
| EP | 0 289 227 | 11/1988 |
| EP | 0 624 584 | 11/1994 |
| FR | 2 696 744 | 4/1994 |
| GB | 2 076 403 | 12/1981 |
| GB | 2 210 366 | 6/1989 |
| JP | 7-138230 | 5/1995 |
| WO | WO 86/04584 | 8/1986 |
| WO | WO 91/07967 | 6/1991 |
| WO | WO 92/04338 | 3/1992 |
| WO | WO 9315062 | 8/1993 |
| WO | WO 95/04051 | 2/1995 |
| WO | WO 9723466 | 7/1997 |
| WO | WO 98/28270 | 7/1998 |
| WO | WO 98/28275 | 7/1998 |
| WO | WO 99/33806 | 7/1999 |

(Continued)

OTHER PUBLICATIONS

Nortey et al. Bioorganic & Medicinal Chemistry letters, vol. 11, p. 1741-1743 (2001).*

(Continued)

*Primary Examiner*—Emily Bernhardt
(74) *Attorney, Agent, or Firm*—Jacqueline M. Cohen

(57) ABSTRACT

Compounds of general formula I $R^1$ is selected from any one of phenyl, pyridinyl, thienyl, furanyl, imidazolyl, pyrrolyl, triazolyl, thiazolyl, and pyridine N-oxide; $R^2$ is independently selected from ethyl and isopropyl; $R^3$ is independently selected from hydrogen and fluoro; $R^4$ is independently selected from —OH, —$NH_2$ and —$NHSO_2R^5$; and $R^5$ is independently selected from hydrogen, —$CF_3$ and $C_1$–$C_6$ alkyl, or salts thereof or separate enantiomers and salts thereof; where each $R^1$ heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the heteroaromatic ring may take place in any position on said ring systems; are disclosed and claimed in the present application, as well as separate enantiomers of the compounds and salts and pharmaceutical compositions comprising the novel compounds and their use in therapy, in particular in the management of pain, anxiety and functional gastrointestinal disorders.

9 Claims, No Drawings

FOREIGN PATENT DOCUMENTS

WO   01/74805   * 10/2001

OTHER PUBLICATIONS

Snyder et al. Trends in Pharmacological Sciences, vol. 24, p. 198-205 (2003).*

Bilsky, et al., SNC 80, A Selective, Nonpeptidic and Systemically Active Opioid Delta Agonist, J. Pharmacol. Experi. Ther. 273:359-366(1995).

Takemori, et al., "Selective Natrexone-Drived Opioid Receptor Antagonists," Annu. Rev. Pharmacol. Toxicol. 32:239-269 (1992).

Bilsky, et al., "Characterization of Enantiomers of (+) BW373U86 and Related Compounds: Highly Selective Non-Peptidic Delta Opioid Agonists," Reg. Peptides 54:25-26 (1994).

Calderon, et al., "Probes for Narcotic Receptor Mediated Phenomena. 19. Synthesis of . . . Opioid Receptor Agonist," J. Med. Chem. 37:2125-2128 (1994).

Calderon, et al., "Probes for Narcotic Receptor Mediated Phenomena. 23. Synthesis . . . Opioid Receptor Ligands," J. Med. Chem. 40:695-704 (1997).

Chang, et al., "A Novel, Potent and Selective Nonpeptidic Delta Opioid Receptor Agonist BW373U86," J. Pharmacol. Exper. Therap. 267:852-857 (1993).

Katrizky, et al., "Benzotriazole-Mediated Arylalkylation and Heteroarylalkylation," Chem. Soc. Rev. 23:363-442 (1994).

Kingsbury, et al., "Synthesis of Structural Analogs of Leukotriene B and their Receptor Binding Activity," J. Med. Chem. 36:3308-3320 (1993).

Lopez, et al., "Exploring the Structure-Activity Relationships . . . Opioid Receptor Nonpeptide Agonist Ligand," J. Med. Chem. 42:5359-5368 (1999).

Plobeck, et al., "New Diarylmethylpiperazines as Potent and Selective Nonpeptidic Opioid Receptor Agonists with Increased In Vitro Metabolic Stability," J. Med. Chem. 43:3878-3894 (2000).

Snuggs, et al., "Facile Synthesis of 8-Substituted Quinolines," J. Org. Chem. 45:1514-1515 (1980).

Zhang, et al., "Probes for Narcotic Receptor Mediated Phenomena. 26. Synthesis . . . Opioid Receptor Ligands," J. Med. Chem. 42:5455-5463 (1999).

English Abstract for FR 2696744 (Apr. 1994).

English Abstract for DE 2900810 (Jul. 1980).

English Abstract for JP 07138230 (May 1995).

Burkey, et al., "The Efficacy of Delta-Opioid Receptor-Selective Drugs," Medline Abstract for Life Sci. 62:1531-1536 (1998).

Nagase, et al., "the Pharmacological Profile of Delta Opioid Receitor Ligands, (+) and (−) TAN-67 on Pain Modulation," Medline Abstract for Life Sci. 68:2227-2231 (2001).

Green, "Protective Groups in Organic Synthesis," pp. 267-268 and 331 (1981).

* cited by examiner

4(PHENYL-PIPERAZINYL-METHYL) BENZAMIDE DERIVATIVES AND THEIR USE FOR THE TREATMENT OF PAIN ANXIETY OR GASTROINTESTINAL DISORDERS

CROSS-REFERENCE TO RELATED APPLICATIONS

This application is a U.S. National Stage of International Application No. PCT/SE02/00956 that was filed on May 16, 2002. The International Application claims priority under 35 U.S.C. § 119(a) to Swedish Application No. 0101772-2 filed May 18, 2001 and Swedish Application No. 0103820-7 filed Nov. 15, 2001.

FIELD OF THE INVENTION

The present invention is directed to novel compounds, to a process for their preparation, their use and pharmaceutical compositions comprising the novel compounds. The novel compounds are useful in therapy, and in particular for the treatment of pain, anxiety and functional gastrointestinal disorders.

BACKGROUND OF THE INVENTION

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., *Journal of Pharmacology and Experimental Therapeutics*, 273(1), pp. 359–366 (1995)). There is however still a need for selective δ-agonists having not only improved selectivity, but also an improved side-effect profile.

Thus, the problem underlying the present invention was to find new analgesics having improved analgesic effects, but also with an improved side-effect profile over current μ agonists, as well as having improved systemic efficacy.

Analgesics that have been identified and are existing in the prior art have many disadvantages in that they suffer from poor pharmacokinetics and are not analgesic when administered by systemic routes. Also, it has been documented that preferred δ agonist compounds, described within the prior art, show significant convulsive effects when administered systemically.

We have now found certain compounds that exhibit surprisingly improved properties, i.a. improved δ-agonist potency, in vivo potency, pharmacokinetic, bioavailability, in vitro stability and/or lower toxicity.

OUTLINE OF THE INVENTION

The novel compounds according to the present invention are defined by the formula I

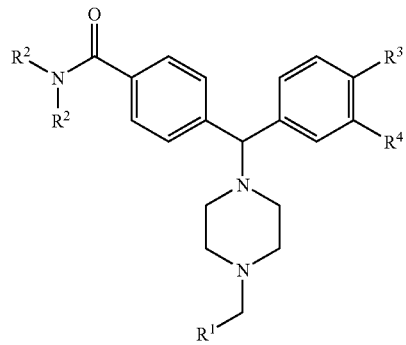

wherein
$R^1$ is selected from any one of (i) phenyl;

(ii) pyridinyl

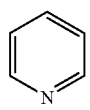

(iii) thienyl

(iv) furanyl

(v) imidazolyl

(vi) triazolyl

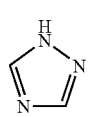

(vii) pyrrolyl

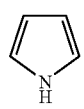

-continued (viii) thiazolyl

(ix) pyridyl-N-oxide

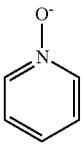

wherein each $R^1$ heteroaromatic ring may optionally and independently be further substituted by 1, 2 or 3 substituents selected from straight and branched $C_1$–$C_6$ alkyl, halogenated $C_1$–$C_6$ alkyl, $NO_2$, $CF_3$, $C_1$–$C_6$ alkoxy, chloro, fluoro, bromo, and iodo;

$R^2$ is independently selected from ethyl and isopropyl;
$R^3$ is independently selected from hydrogen and fluoro;
$R^4$ is independently selected from —OH, —$NH_2$ and —$NHSO_2R^5$; and
$R^5$ is independently selected from hydrogen, —$CF_3$ and $C_1$–$C_6$ alkyl, provided that when $R^2$ is ethyl and $R^3$ is hydrogen then $R^4$ cannot be —OH.

The substitutions on the heteroaromatic ring may take place in any position on said ring systems.

When the $R^1$ phenyl ring and the $R^1$ heteroaromatic ring(s) are substituted, the preferred substituents are selected from any one of $CF_3$, methyl, iodo, bromo, fluoro and chloro, of which methyl is most preferred.

A further embodiment of the present invention is thus a compound according to formula I wherein $R^1$ is as defined above and each $R^1$ phenyl ring and $R^1$ heteroaromatic ring may independently be further substituted by a methyl group;

A further embodiment of the present invention is a compound according to FIG. 1 wherein $R^1$ is phenyl, pyrrolyl, furanyl, thienyl or imidazolyl; $R^2$ is ethyl or isopropyl; $R^3$ is hydrogen or fluoro; $R^4$ is —$NH_2$ or —$NHSO_2R^5$; and $R^5$ is $C_1$–$C_6$ alkyl, optionally with 1 or 2 of the preferred substituents on the R phenyl or R heteroaromatic ring.

An additional embodiment of the present invention is a compound according to FIG. 1 wherein $R^1$ is phenyl, pyrrolyl, furanyl, thienyl or imidazolyl; $R^2$ is ethyl or isopropyl; $R^3$ is hydrogen; $R^4$ is —$NHSO_2R^5$; and $R^5$ is $C_1$–$C_6$ alkyl, optionally with 1 or 2 of the preferred substituents on the $R^1$ phenyl or $R^1$ heteroaromatic ring.

Other embodiments of the present invention are compounds according to FIG. 1 wherein a) $R^1$ is phenyl, pyrrolyl, or furanyl; $R^2$ is ethyl or isopropyl; $R^3$ is hydrogen or fluoro; and $R^4$ is —$NH_2$; b) $R^1$ is thienyl or imidazolyl; $R^2$ is ethyl or isopropyl; $R^3$ is hydrogen or fluoro; and $R^4$ is —$NH_2$; c) $R^1$ is phenyl, pyrrolyl, furanyl, thienyl or imidazolyl; $R^2$ is ethyl or isopropyl; $R^3$ is hydrogen or fluoro; $R^4$ is —$NHSO_2R^5$; and $R^5$ is $C_1$–$C_6$ alkyl; and d) $R^1$ is phenyl, pyrrolyl, furanyl, thienyl or imidazolyl; $R^2$ is ethyl or isopropyl; $R^3$ is hydrogen or fluoro; $R^4$ is —$NHSO_2R^5$; and $R^5$ is $C_1$–$C_6$ alkyl, wherein all embodiments a) to d) may optionally be substituted with 1 or 2 of the preferred substituents on the $R^1$ phenyl or $R^1$ heteroaromatic ring.

Within the scope of the invention are also separate enantiomers and salts of the compounds of the formula I, including salts of enantiomers. Also within the scope of the present invention are mixtures of the separate enantiomers, such as the racemic mixuture, as well as salts of mixtures of separate enantiomers.

Separation of racemic mixtures into separate enantiomers is well known in the art and may be accomplished for example by separation on a suitable chiral chromatography column. Preparation of salts is well known in the art, and may be accomplished for example by mixing a compound of formula I in a suitable solvent with the desired protic acid and isolation by means standard in the art. Salts of compounds of formula I include pharmaceutically acceptable salts and also pharmaceutically unacceptable salts.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety and stress-related disorders such as post-traumatic stress disorders, panic disorder, generalized anxiety disorder, social phobia, and obesessive compulsive disorder; urinary incontinence, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Methods of Preparation

The compounds of the present invention can be prepared using the following general procedure.

Preparation of Phenols

EXAMPLES 1–3

The compounds of formula I wherein $R^4$ is —OH is prepared by reacting a compound of the general formula II

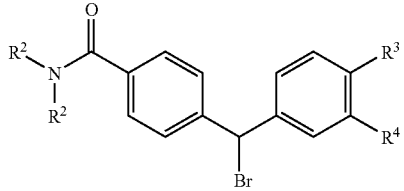

II wherein $R^2$ and $R^3$ are as defined in FIG. 1 and $R^4$ is OMe, with Boc-piperazine in acetonitrile in the presence of triethylamine under standard conditions, followed by removal of the Boc protection group under standard conditions to give a compound of the Formula III

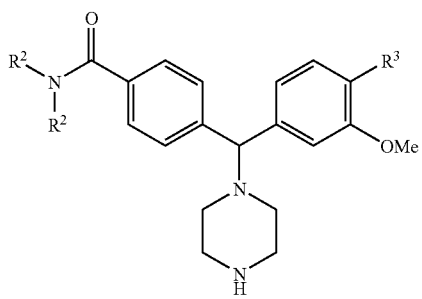

III which is thereafter alkylated under reductive conditions with a compound of the Formula $R^1$—CHO, followed by cleavage of the methyl ether using $BBr_3$ in dichloromethane to give a compound of the Formula I wherein $R^4$ is —OH.

Preparation of Anilines

EXAMPLES 4–6

The compound of formula I wherein $R^4$ is —NH$_2$ is prepared by reacting a compound of the general formula IV

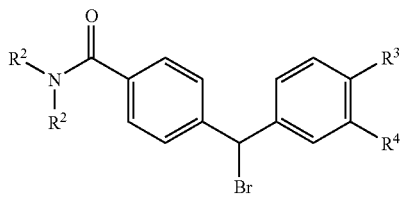

IV wherein $R^2$ and $R^3$ are as defined in FIG. 1 and $R^4$ is NO$_2$, with Boc-piperazine in acetonitrile in the presence of triethylamine under standard conditions, followed by removal of the Boc protection group under standard conditions to give a compound of the Formula V

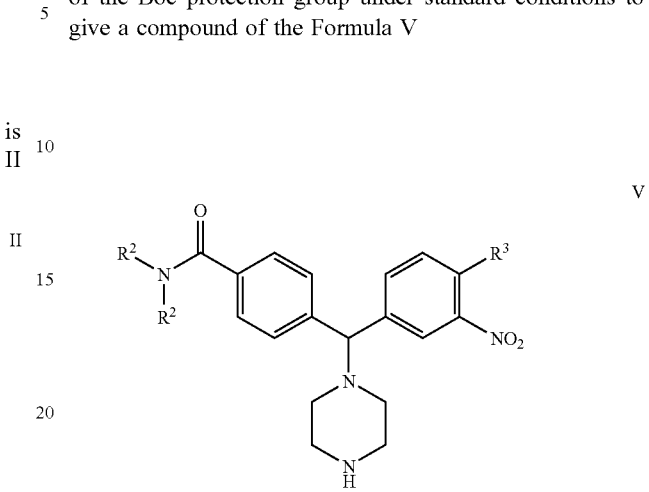

V which is thereafter alkylated under reductive conditions with a compound of the Formula $R^1$—CHO, followed by reduction of the nitro group using hydrogen and palladium on charcoal to give a compound of the Formula I wherein $R^4$ is —NH$_2$.

Preparation of Methyl Sulfonanilides

EXAMPLES 7–8

The compound of formula I wherein $R^4$ is —NHSO$_2$R$^5$ is prepared by reacting a compound of the general formula VI

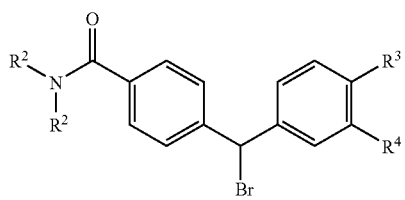

VI wherein $R^2$ and $R^3$ are as defined in claim 1 and $R^4$ is NO$_2$, with Boc-piperazine in acetonitrile in the presence of triethylamine under standard conditions, followed reduction of the nitro group by hydrogenolysis using palladium on charcoal as the catalyst, metanesulphonylation using methanesulphonylanhydride in dichloromethane in the presence of triethylamine, and thereafter removal of the Boc protection group under standard conditions to give a compound of the Formula VII

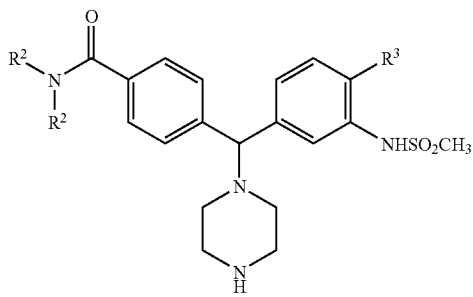

which is thereafter alkylated under reductive conditions with a compound of the Formula $R^1$—CHO, followed by reduction of the nitro group using hydrogen and palladium on charcoal to give a compound of the Formula I wherein $R^4$ is —$NHSO_2R^5$.

Within the scope of the invention are also separate enantiomers and salts of the compounds of the Formula I, including salts of enantiomers. Compounds of Formula I are chiral compounds, with the diarylmethylpiperazine group being the stereogenic center, see FIG. 1 * below.

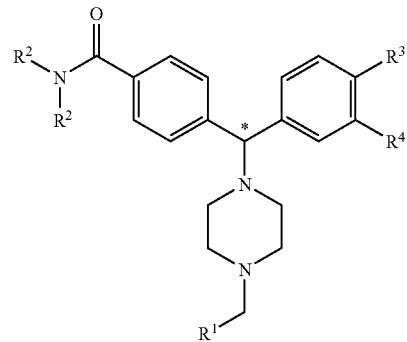

A further embodiment of the present invention is thus the (−)-enantiomer of a compound according to Formula I, as well as a salt of said compound.

A further embodiment of the present invention is thus the (+)-enantiomer of a compound according to Formula I, as well as a salt of said compound.

EXAMPLES

The invention will now be described in more detail by the following Examples, which are not to be construed as limiting the invention.

Scheme 1:
Preparation of Fluoro Phenols; Examples 1–3

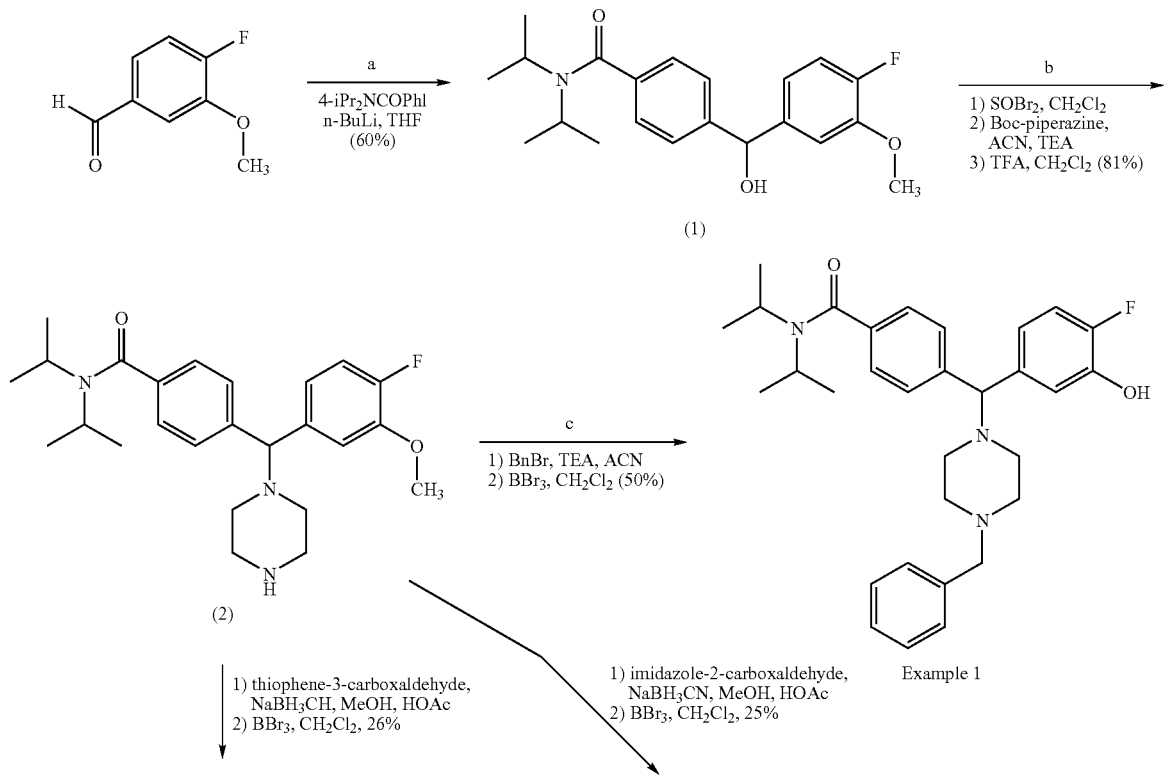

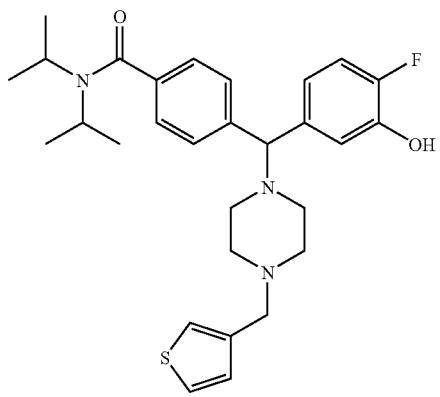

Example 2

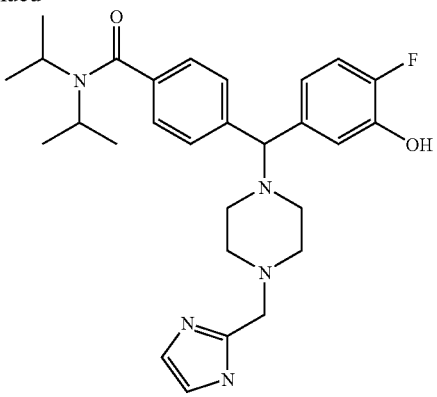

Example 3

Intermediate 1

4-[(4-fluoro-3-methoxyphenyl)hydroxy)methyl]-N,N-diisopropyl-benzamide

N,N-Diisopropyl-4-iodobenzamide (6.0 g, 18 mmol) was dissolved in THF (200 mL) and cooled to −78° C. under nitrogen atmosphere. n-BuLi (14 mL, 1.3 M solution in hexane, 18 mmol) was added dropwise during 10 min at −65 to −78° C. 4-fluoro-3-methoxybenzaldehyde (2.8 g, 18 mmol) was added dropwise dissolved in THF (5 mL). $NH_4Cl$ (aq.) was added after 30 min. After concentration in vacuo, extraction with EtOAc/water, drying ($MgSO_4$) and evaporation of the organic phase, the residue was purified by chromatography on silica (0–75% EtOAc/heptane) to yield the desired product (3.9 g, 60%). $^1H$ NMR ($CDCl_3$) δ 1.0–1.6 (m, 12H), 2.65 (d, J=4 Hz, 1H), 3.4–3.9 (m, 2H), 3.80 (s, 3H), 6.10 (d, J=4 Hz, 1H), 6.76 (m, 1H), 6.95 (m, 1H), 7.04 (m, 1H), 6.76 (m, 1H), 7.25, 7.40 (2d, J=7.5 Hz, 4H).

Intermediate 2

4-[(4-fluoro-3-methoxyphenyl)(1-piperazinyl)methyl]-N,N-diisopropylbenzamide Intermediate 1 (3.9 g, 11 mmol) was dissolved in dry $CH_2Cl_2$ (50 mL) and treated with $SOBr_2$ (0.88 mL, 11 mmol) at 0 to 25° C. for 30 min. Neutralization with $KHCO_4$ (aq.) and drying ($K_2CO_4$) of the organic phase was followed by solvent evaporation in vacuo. The residue and $Et_3N$ (1.8 mL, 13 mmol) was dissolved in MeCN (50 mL) and stirred with Boc-piperazine (2.1 g, 11 mmol) at 25° C. for 12 h. Concentration in vacuo and chromatography on silica (0 to 50% EtOAc in heptane) gave 4.6 g. 1.6 g was treated with TFA in $CH_2Cl_2$ (1:1), concentrated in vacuo, extracted $CH_2Cl_2/K_2CO_4$ (aq.), dried ($K_2CO_4$) and evaporated in vacuo to give Intermediate 2 (1.3 g, 81% from intermediate 1). MS (ES) 428.21 (MH+).

Example 1

4-[1-(4-Benzyl-piperazin-1-yl)-1-(4-fluoro-3-hydroxy-phenyl)-methyl]-N,N-diisopropyl-benzamide Intermediate 2 (0.41 g, 0.96 mmol) and triethylamine (0.20 mL, 1.4 mmol) were dissolved in MeCN (10 mL).

Benzyl bromide (0.14 mL, 1.1 mmol) was added with stirring at 25° C. After 12 h the solution was concentrated and purified by reverse phase chromatography (LiChroprep RP-18, 10–80% MeCN in water, 0.1% TFA). 0.53 g of free base was obtained after extraction with $CH_2Cl_2/K_2CO_4$ (aq.), drying ($K_2CO_4$) and evaporation in vacuo. Treatment with boron tribromide (4 eq., 1M solution in $CH_2Cl_2$) in $CH_2Cl_2$ at −78° C., addition of water, concentration in vacuo and reverse phase chromatography gave Example 1 as the trifluoroacetate (0.35 g, 50%). MS (ES) 504.22 (MH+). IR (NaCl) 3222, 1677, 1592, 1454, 1346, 1201, 1135 (cm-1). $^1H$ NMR ($CD_3OD$) δ=1.1, 1.5 (m, 12H), 2.3 (m, 3H), 2.9–3.8 (m, 7H), 4.33 (s, 2H), 4.75 (s, 1H), 6.60 (m, 1H), 6.83 (m, 1H), 6.94 (m, 1H), 7.24 (d, J=8 Hz, 2H), 7.47 (m, 7H). Anal. Calc. for $C_{31}H_{38}FN_3O_2 \times 0.8 C_4H_2F_6O_4$ C:59.87, H:5.82, N:6.12. Found C:60.06, H:5.83, N:6.19.

Example 2

4-[1-(4-Fluoro-3-hydroxy-phenyl)-1-(4-thiophen-3-ylmethyl-piperazin-1-yl)-methyl]-N,N-diisopropyl-benzamide Intermediate 2 (0.43 g, 1.0 mmol) was dissolved in MeOH (5 mL) with 3-thiophene-carboxaldehyde (0.11 mL, 1.2 mmol) and HOAc (57 µL, 1.0 mmol) and stirred for 1 h. Sodium cyanoborohydride (63 mg, 1.0 mmol) was added in portions over 6 h and the reaction was stirred at 25° C. for an additional 12 h before working up by concentration in vacuo and extraction ($CH_2C_2/K_2CO_3$(aq)). Purification by reverse phase chromatography as for Example 1 to give 0.32 g (0.62 mmol) as free base. Treatment with boron tribromide as for Example 1 and chromatography gave Example 2 (0.20 g, 26%) as the trifluoroacetate. MS (ES) 510.17 (MH+). IR (NaCl) 3281, 1674, 1606, 1454, 1346, 1200, 1135 (cm-1). $^1H$ NMR ($CD_3OD$) δ=1.1, 1.5 (m, 12H), 2.30 (m, 2H), 2.9–3.7 (m, 10H), 4.37 (s, 2H), 4.75 (s, 1H), 6.60 (m, 1H), 6.84 (m, 1H), 6.94 (m, 1H), 7.18 (m, 1H), 7.25, 7.48 (2d, J=8.0 Hz, 4H), 7.55 (m, 1H), 7.65 (m, 1H). Anal. Calc. for $C_{29}H_{36}FN_3O_2S \times 0.8 C_4H_2F_6O_4 \times 0.5 H_2O$, C:55.16, H:5.55, N:5.99. Found, C:55.12, H:5.39, N:6.07.

Example 3

4-{1-(4-Fluoro-3-hydroxy-phenyl)-1-[4-(1H-imidazol-2-ylmethyl)-piperazin-1-yl]-methyl}-N,N-diisopropyl-benzamide Employing the same procedure as for Example 2 reaction with 2-imidazole-carboxaldehyde (0.10 g, 1.11 mmol) followed by treatment with boron tribromide (6 eq.) gave Example 3 (0.18 g, 25%) as the trifluoroacetate. MS (ES) 494.23 (MH+). IR (NaCl) 3123, 1673, 1592, 1454, 1350, 1201, 1135 (cm-1). $^1$H NMR (CD$_3$OD) δ=1.1, 1.5 (m, 12H), 2.7–3.8 (m, 10H), 3.95 (s, 2H), 5.20 (m, 1H), 6.70 (m, 1H), 6.94 (m, 1H), 7.02 (m, 1H), 7.32, 7.58 (2d, J=8.0 Hz, 4H), 7.46 (s, 1H). Anal. Calc. for C$_{28}$H$_{36}$FN$_5$O$_2$×1.2 C$_4$H$_2$F$_6$O$_4$×0.7 H$_2$O, C:50.51, H:5.14, N:8.98. Found, C:50.44, H:5.18, N:9.11.

Scheme 2:
Preparation of Anilines; Examples 4–6

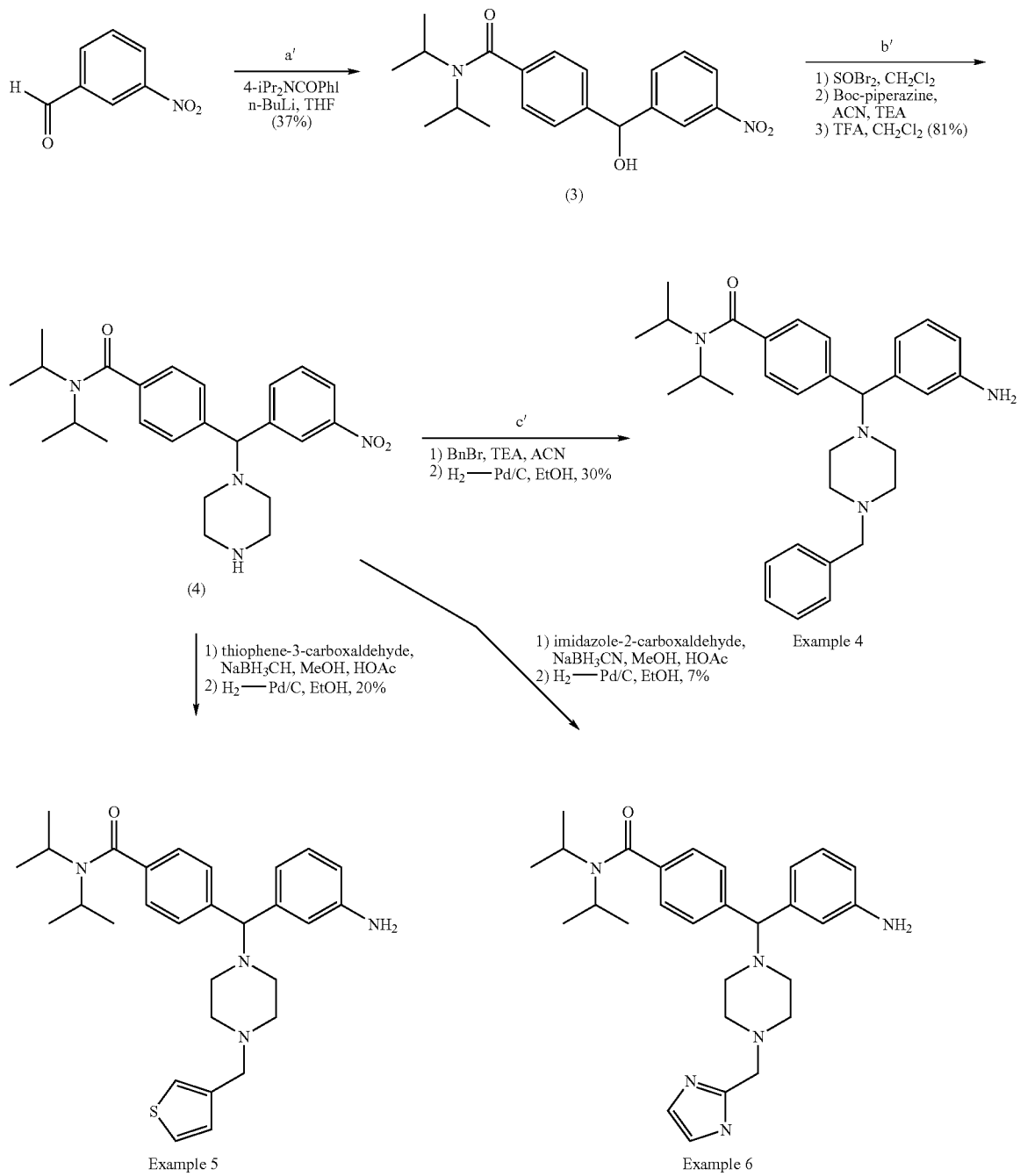

Intermediate 3

4-[hydroxy(3-nitrophenyl)methyl]-N,N-diisopropyl-benzamide

Procedure as for intermediate 1 but after addition of n-BuLi the solution was cannulated into a solution of 3-nitrobenzaldehyde (2.7 g, 18 mmol) in toluene/THF (approx. 1:1, 100 mL) at −78° C. Workup and chromatography gave for intermediate 3 (2.4 g, 37%). $^1$H NMR (CDCl$_3$) δ 1.1–1.7 (m, 12H), 3.90 (d, J=3.5 Hz, 1H), 3.4–3.9 (m, 2H), 5.91 (s, J=3.5 Hz, 1H), 7.27, 7.35 (2d, J=8 Hz, 4H), 7.51 (m, 1H), 7.71 (m, 1H), 8.13 (m, 1H), 8.30 (s, 1H).

Intermediate 4

N,N-diisopropyl-4-[(3-nitrophenyl)(1-piperazinyl)methyl]benzamide

Employing the same procedure as for intermediate 2, intermediate 3(2.4 g, 6.7 mmol) gave Boc-protected intermediate 4 (2.83 g, 81%). TFA treatment quantitatively gave intermediate 4, MS (ES) 425.23 (MH+).

Example 4

4-[1-(3-Amino-phenyl)-1-(4-benzyl-piperazin-1-yl)-methyl]-N,N-diisopropyl-benzamide Reaction of 7 (0.40 g, 0.94 mmol) with benzyl bromide as for Example 1 was followed by hydrogenation (H$_2$, 40 psi) with 10% Pd/C (50 mg) in EtOH (25 mL) and 2 N HCl (1.2 mL, 2.4 mmol) for 2 h. Purification by reverse phase chromatography using the same conditions as for Example 1 gave Example 4 (0.20 g, 30%) as the trifluoroacetate. MS (ES) 485.40 (MH+). IR (NaCl) 3414, 1673, 1605, 1455, 1345, 1201, 1134 (cm-1). $^1$H NMR (CD$_3$OD) δ=1.1, 1.5 (m, 12H), 2.3 (m, 2H), 2.9–3.8 (m, 8H), 4.31 (s, 2H), 4.47 (s, 1H), 7.02 (m, 1H), 7.21–7.52 (m, 12H). Anal. Calc. for C$_{31}$H$_{40}$N$_4$O×1.2 C$_4$H$_2$F$_6$O$_4$×0.5 H$_2$O, C:56.04, H:5.70, N:7.30. Found, C:56.06, H:5.67, N:7.41.

Example 5

4-[1-(3-Amino-phenyl)-1-(4-thiophen-3-ylmethyl-piperazin-1-yl)-methyl]-N,N-diisopropyl-benzamide Reaction of intermediate 4 (0.40 g, 0.94 mmol) with 3-thiophene-carboxaldehyde as for example 2 was followed by hydrogenation (H$_2$, 30 psi) with 10% Pd/C (50 mg) in EtOH (25 mL) and 2 N HCl (1.0 mL, 2.0 mmol) for 12 h. Purification by reverse phase chromatography using the same conditions as for Example 1 gave Example 5 (0.13 g, 20%) as the ditrifluoroacetate. MS (ES) 491.28 (MH+). IR (NaCl) 3408, 1673, 1605, 1455, 1345, 1201, 1134 (cm-1). $^1$H NMR (CD$_3$OD) δ=1.1, 1.5 (m, 12H), 2.3 (m, 2H), 2.9–3.8 (m, 8H), 4.35 (s, 2H), 4.44 (s, 1H), 6.98 (m, 11), 7.167.32 (m, 6H), 7.49 (d, J=8 Hz, 2H), 7.55 (m, 1H), 7.64 (m, 1H). Anal. Calc. for C$_{29}$H$_{38}$N$_4$OS×1.3 C$_4$H$_2$F$_6$O$_4$×0.6 H$_2$O, C:51.48, H:5.28, N:7.02. Found, C:51.51, H:5.20, N:7.01.

Example 6

4-{1-(3-Amino-phenyl)-1-[4-(1H-imidazol-2-ylmethyl)-piperazin-1-yl]-methyl}-N,N-diisopropyl-benzamide Employing the same procedure as for Example 2, reaction of intermediate 4 with 2-imidazole-carboxaldehyde (0.10 g, 1.1 mmol) followed by hydrogenation gave Example 6 (45 mg, 7%) as ditrifluoroacetate salt. MS(ES) 475.30 (MH+). IR (2×TFA, NaCl) 3351, 1674, 1621, 1455, 1349, 1202, 1134 (cm-1). $^1$H NMR (2×TFA, CD$_3$OD) δ=1.1, 1.5 (m, 12H), 2.9–3.8 (m, 8H), 4.35 (s, 2H), 4.44 (s, 1H), 6.98 (m, 1H), 7.16–7.32 (m, 6H), 7.49 (d, J=8 Hz, 2H), 7.55 (m, 1H), 7.64 (m, 1H). Anal. Calc. for C$_{28}$H$_{38}$N$_6$O×1.6 C$_4$H$_2$F$_6$O$_4$× 0.8 H$_2$O, C:48.39, H:5.05, N:9.84. Found, C:48.43, H:5.06, N:9.85.

Scheme 3:
Preparation of Methyl Sulfonanilides; Examples 7–8

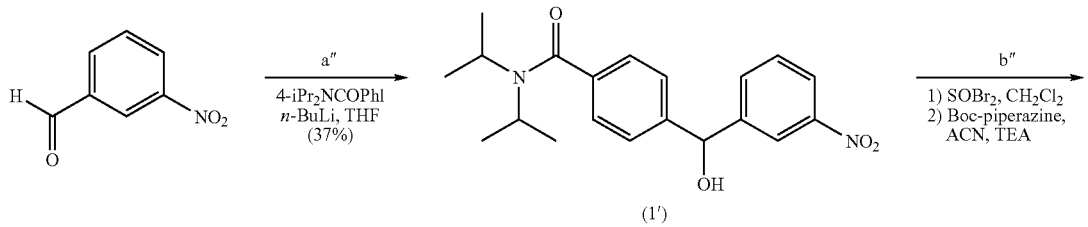

-continued

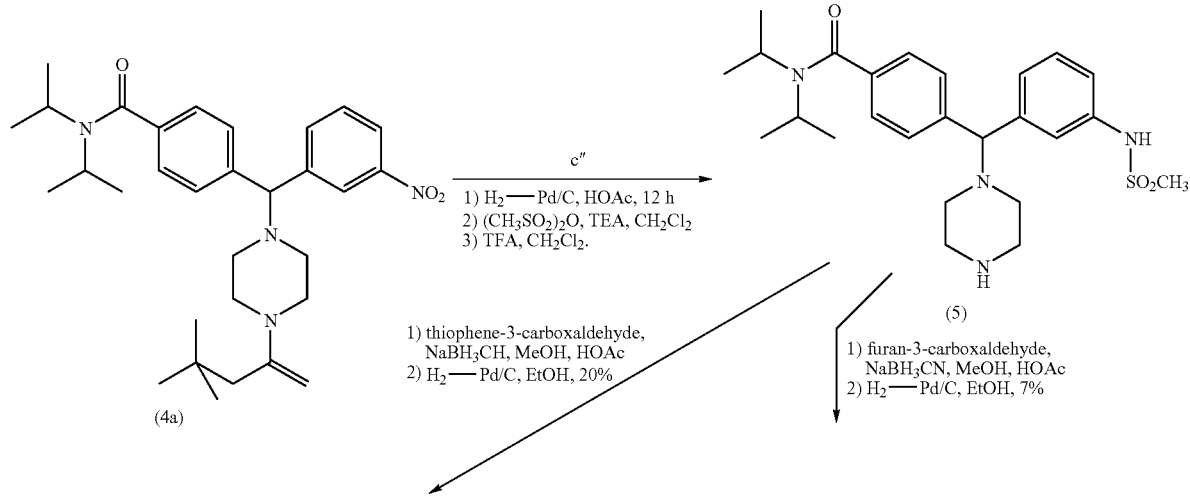

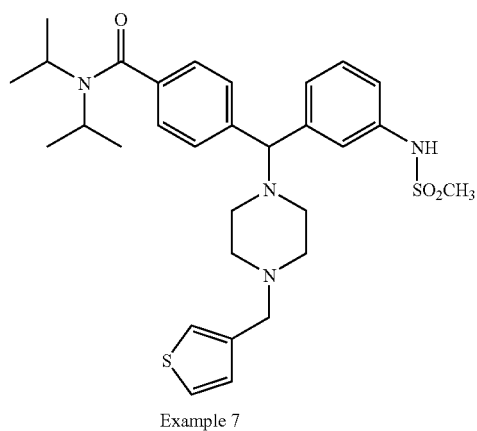

Example 7

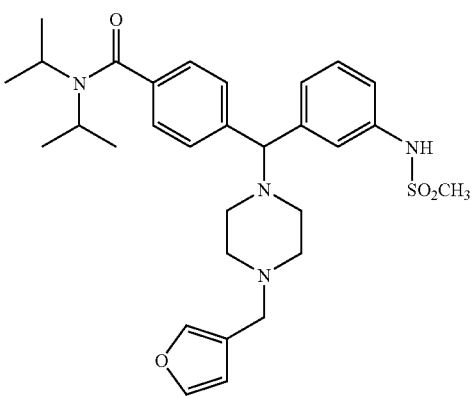

Example 8

Intermediate 5

N,N-diisopropyl-4-[{3-[(methylsulfonyl)amino]phenyl}(1-piperazinyl)methyl]benzamide Intermediate 3 gave Boc-protected Intermediate 4 as described for Intermediate 4, above. Boc-protected Intermediate 4 (1.21 g, 2.3 mmol) was hydrogenated under $H_2$ at 30 psi with 10% Pd/C (150 mg) in AcOH (25 mL) for 12 h. Evaporation in vacuo and extraction with $CH_2Cl_2/K_2CO_3$ (aq.) gave 1.1 g (2.3 mmol) of the intermediate aniline, which was dissolved in $MeCN/CH_2Cl_2$ (1:1, 10 mL). $Et_3N$ (0.48 mL, 3.4 mmol), then methanesulponylanhydride (0.41 g, 2.4 mmol) was added at 0° C. After warming to room temperature the reaction was worked up by extraction $CH_2Cl_2$/brine. Purification by chromatography on silica (0–5% $MeOH/CH_2Cl_2$) gave Boc-protected Intermediate 5 (1.3 g, 97%). Treatment with TFA in $CH_2Cl_2$ quantitatively gave Intermediate 5. MS (ES) 473.16 (MH+).

Example 7

N,N-Diisopropyl-4-[1-(3-methanesulfonylaminophenyl)-1-(4-thiophen-3-ylmethyl-piperazin-1-yl)-methyl]-benzamide Reductive amination procedure as for Example 2. Intermediate 5 (0.20 g, 0.43 mmol) gave Example 7 (90 mg, 26%) as ditrifluoroacetate salt. The dihydrochloride salt was obtained after extraction of the free base with $CH_2Cl_2$/ $K_2CO_3$ (aq.) and treatment with 2 eq. HCl (aq.). MS (ES) 569.21 (MH+). IR (free base, NaCl) 1604, 1455, 1340, 1151 (cm-1). $^1$H NMR (free base, $CDCl_3$) δ=0.9–1.7 (m, 12H), 2.5 (m, 8H), 2.85 (s, 3H), 3.55 (s, 2H), 3.8 (m, 2H), 4.22 (s, 1H), 7.00–7.40 (m, 12H). Anal. Calc. for $C_{30}H_{40}N_4O_3S_2 \times$ 2.6 HCl, C:54.30, H:6.47, N:8.44. Found, C:54.33, H:6.20, N:8.32.

Example 8

4-([4-(3-furylmethyl)-1-piperazimyl]{3-[(methylsulfonyl)amino]phenyl}-N,N-diisopropyl-benzamide Employing the same procedure as for Intermediate 7. Intermediate 5 (0.21 g, 0.45 mmol) gave Example 8 (80 mg, 32%) as free base. MS (ES) 553.23 (MH+). IR (free base, NaCl) 1604, 1455, 1340, 1151 (cm-1). $^1$H NMR (free base, CDCl$_3$) δ=1.0–2.6(m, 20H), 2.91 (s, 3H), 3.40 (s, 2H), 4.22 (s, 1H), 6.39 (s, 1H), 7.06–7.42 (m, 11H). Anal. Calc. for C$_{30}$H$_{40}$N$_4$O$_4$S×2.8 HCl, C:55.03, H:6.59, N:8.56. Found, C:54.93, H:5.93, N:8.49.

matography on silica gave the 3-thienylmethyl derivative (0.45 g, 43%). Hydrogenation of the product (0.30 g, 0.61 mmol) and reverse phase chromatography gave the title compound (0.17 g, 35%) as the tris-trifluoroacetate. MS (ES) 463.34 (MH+). IR (NaCl) 3418, 1673, 1600, 1461, 1200, 1135 (cm-1). $^1$H NMR (CD$_3$OD) δ=1.17, 1.31 (m, Scheme 4:
Preparation of Examples 9–11

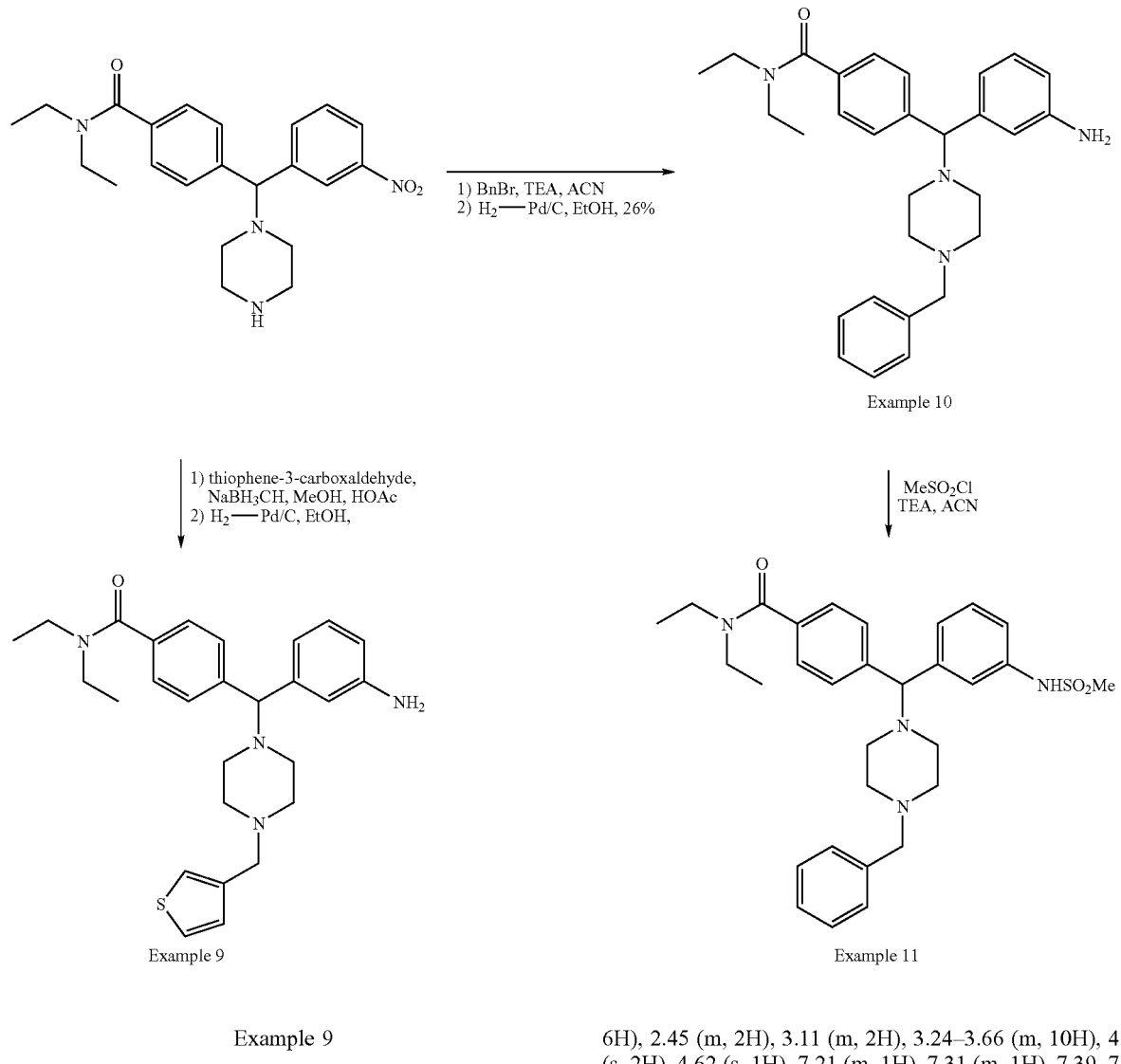

Example 10

Example 9

Example 11

Example 9

4-{(3-aminophenyl)[4-(3-thienylmethyl)-1-piperazinyl]methyl}-N,N-diethylbenzamide N,N-diethyl-4-[(3-nitrophenyl)(1-piperazinyl)methyl]benzamide (prepared analogous to intermediate (4) in Scheme 2) (0.85 g, 2.1 mmol) was dissolved in MeOH (5 mL) with 3-thiophenecarboxaldehyde (0.40 mL, 4.3 mmol) and HOAc (60 μL, 1.0 mmol) and stirred for 1 h. Sodium cyanoborohydride (135 mg, 2.1 mmol) was added in portions over 6 h and the reaction was stirred at 25° C. for an additional 12 h before working up by concentration in vacuo and extraction (CH$_2$Cl$_2$/K$_2$CO$_3$(aq)). Purification by chro- 6H), 2.45 (m, 2H), 3.11 (m, 2H), 3.24–3.66 (m, 10H), 4.47 (s, 2H), 4.62 (s, 1H), 7.21 (m, 1H), 7.31 (m, 1H), 7.39–7.56 (m, 5H), 7.61–7.68 (m, 3H), 7.77 (m, 1H).

Example 10

4-[(3-aminophenyl)(4-benzyl-1-piperazinyl)methyl]-N,N-diethylbenzamide

N,N-diethyl-4-[(3-nitrophenyl)(1-piperazinyl)methyl]benzamide (1.7 g, 4.3 mmol) and triethylamine (1.2 mL, 8.6 mmol) was dissolved in MeCN (10 mL). Benzyl bromide (0.56 mL, 4.7 mmol) was added with stirring at 25° C. After 12 h the solution was concentrated in vacuo. Extraction (CH$_2$Cl$_2$/K$_2$CO$_3$(aq)) and purification by chromatograpy on silica gave the benzylated product (1.4 g, 2.9 mmol). Hydrogenation (H$_2$, 40 psi) with 10% Pd/C (100 mg) in EtOH (25 mL) and 2 N HCl (2.5 mL, 5 mmol) for 4 h was followed by concentration in vacuo and reverse phase chromatography to give the title compound as the tris-trifluoroacetate (0.9 g, 26%). MS (ES) 457.26 (MH+). IR (NaCl) 3422, 1672, 1603, 1458, 1209, 1133 (cm-1). $^1$H NMR (CD$_3$OD) δ=1.1, 1.2 (m, 6H), 2.3 (m, 2H), 2.9–3.6 (m, 10H), 4.33 (s, 2H), 4.49 (s, 1H), 5.48 (s, 2H), 7.01 (m, 1H), 7.24–7.34 (m, 5H), 7.47 (m, 5H), 7.52 (d, J=7.5 Hz, 2H).

Example 11

4-((4-benzyl-1-piperazinyl){3-[(methylsulfonyl) amino]phenyl}methyl)-N,N-diethylbenzamide The product of Example 10 (0.35 g, 0.76 mmol) and triethylamine (0.12 mL, 0.84 mmol) was dissolved in MeCN (10 mL) and methanesulfonic anhydride (0.14 g, 0.84 mmol) was added at 0° C. After stirring 10 min at 25° C., the solution was concentrated in vacuo and purified by reverse phase chromatography to give the title compound as the bis-trifluoroacetate (0.23 g, 40%). MS (ES) 535.21 (MH+). IR (NaCl) 3479, 1673, 1604, 1458, 1337, 1200, 1150 (cm-1). $^1$H NMR (CD$_3$OD) δ=1.18, 1.31 (m, 6H), 2.41 (m, 2H), 2.98 (s, 3H), 3.13 (m, 21), 3.28–3.65 (m, 8H), 4.44 (s, 2H), 4.57 (s, 1H), 5.57 (d, J=2 Hz, 2H), 7.15 (m, 1H), 7.30 (m, 1H), 7.37 (m, 1H), 7.42 (m, 2H), 7.54–7.60 (m, 6H), 7.63 (m, 2H).

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Salts include, but are not limited to pharmaceutically acceptable salts. Examples of pharmaceutically acceptable salts within the scope of the present invention include: acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc. Examples of pharmaceutically unacceptable salts within the scope of the present invention include: hydroiodide, perchlorate, and tetrafluoroborate. Pharmaceutically unacceptable salts could be of use because of their advantageous physical and/or chemical properties, such as crystallinity.

Preferred pharmaceutically acceptable salts are the hydrochlorides, sulfates and bitartrates. The hydrochloride and sulfate salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Biological Evaluation

In vitro Model

Cell Culture

A. Human 293S cells expressing cloned human μ, δ, and κ receptors and neomycin resistance were grown in suspension at 37° C. and 5% CO$_2$ in shaker flasks containing calcium-free DMEM10% FBS, 5% BCS, 0.1% Pluronic F-68, and 600 µg/ml geneticin.

B. Mouse and rat brains were weighed and rinsed in ice-cold PBS (containing 2.5 mM EDTA, pH 7.4). The brains were homogenized with a polytron for 15 sec (mouse) or 30 sec (rat) in ice-cold lysis buffer (50 mM Tris, pH 7.0, 2.5 mM EDTA, with phenylmethylsulfonyl fluoride added just prior use to 0.5 MmM from a 0.5M stock in DMSO:ethanol).

Membrane Preparation

Cells were pelleted and resuspended in lysis buffer (50 mM Tris, pH 7.0, 2.5 mM EDTA, with PMSF added just prior, to use to 0.1 mM from a 0.1 mM stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g (max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with sodium dodecyl sulfate.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 µg/ml aprotinin, 10 µM bestatin, 10 µM diprotin A, no DTT). Aliquots of 100 µl were added to iced 12×75 mm polypropylene tubes containing 100 µl of the appropriate radioligand and 100 µl of test compound at various concentrations. Total (TB) and nonspecific (NS) binding were determined in the absence and presence of 10 µM naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 µl MS-20 scintillation fluid/well.

Functional Assays

The agonist activity of the compounds is measured by determining the degree to which the compounds receptor complex activates the binding of GTP to G-proteins to which the receptors are coupled. In the GTP binding assay, GTP $[\gamma]^{35}S$ is combined with test compounds and membranes from HEK-293S cells expressing the cloned human opioid receptors or from homogenised rat and mouse brain. Agonists stimulate $GTP[\gamma]^{35}S$ binding in these membranes. The $EC_{50}$ and $E_{max}$ values of compounds are determined from dose-response curves. Right shifts of the dose response curve by the delta antagonist naltrindole are performed to verify that agonist activity is mediated through delta receptors.

Procedure for Rat Brain GTP

Rat brain membranes are thawed at 37° C., passed 3 times through a 25-gauge blunt-end needle and diluted in the GTPγS binding (50 mM Hepes, 20 mM NaOH, 100 mM NaCl, 1 mM EDTA, 5 mM $MgCl_2$, pH 7.4, Add fresh: 1 mM DTT, 0.1% BSA). 120 µM GDP final is added membranes dilutions. The EC50 and Emax of compounds are evaluated from 10-point dose-response curves done in 300 µl with the appropriate amount of membrane protein (20 µg/well) and 100000–130000 dpm of $GTP\gamma^{35}S$ per well (0.11–0.14 nM). The basal and maximal stimulated binding are determined in absence and presence of 3 µM SNC-80

Data Analysis

The specific binding (SB) was calculated as TB-NS, and the SB in the presence of various test compounds was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean ±S.E.M. values of $IC_{50}$, $K_i$ and $n_H$ were reported for ligands tested in at least three displacement curves. Biological activity of the compounds of the present invention is indicated in Table 2.

TABLE 2

| | Biological data. | | | | | |
|---|---|---|---|---|---|---|
| Ex. | HDELTA (nM) | | | RAT BRAIN (nM) | | MOUSE BRAIN (nM) | |
| # | $IC_{50}$ | $EC_{50}$ | % EMax | $EC_{50}$ | % EMax | $EC_{50}$ | % EMax |
| 1–11 | 0.50–13 | 0.32–104 | 94–106 | 2.9–867 | 125–159 | 4.9–1441 | 126–154 |

Receptor Saturation Experiments

Radioligand $K_\delta$ values were determined by performing the binding assays on cell membranes with the appropriate radioligands at concentrations ranging from 0.2 to 5 times the estimated $K_\delta$ (up to 10 times if amounts of radioligand required are feasible). The specific radioligand binding was expressed as pmole/mg membrane protein. Values of $K_\delta$ and $B_{max}$ from individual experiments were obtained from non-linear fits of specifically bound (B) vs. nM free (F) radioligand from individual according to a one-site model.

Determination of Mechano-Allodynia Using Von Frey Testing

Testing was performed between 08:00 and 16:00 h using the method described by Chaplan et is al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold}=10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \; MPE = \frac{\text{Drug treated threshold (g)} - \text{allodynia threshold (g)}}{\text{Control threshold (g)} - \text{allodynia threshold (g)}} \times 100$$

Administration of Test Substance

Rats were injected (subcutaneously, intraperitoneally, intravenously or orally) with a test substance prior to von Frey testing, the time between administration of test compound and the von Frey test varied depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1–100 μmol/kg.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

For the anxiety and anxiety-like indications, efficacy has been established in the geller-seifter conflict test in the rat.

For the functional gastrointestina disorder indication, efficacy can be established in the assay described by Coutinho SV et al, in American Journal of Physiology—Gastrointestinal & Liver Physiology. 282(2):G307–16, 2002 February, in the rat.

The invention claimed is:

1. A method for the treatment of anxiety, comprising administering to a subject suffering from anxiety an effective amount of a compound of the formula I

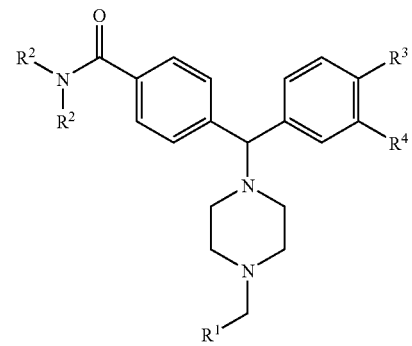

wherein
R¹ is selected from any one of (i) phenyl

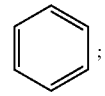
;

(ii) pyridinyl

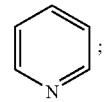
;

(iii) thienyl

;

-continued (iv) furanyl

;

(v) imidazolyl

;

(vi) triazolyl

;

(vii) pyrrolyl

;

(viii) thiazolyl

;

(ix) pyridyl-N-oxide

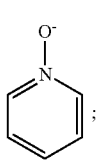;

wherein each $R^1$ phenyl and $R^1$ heteroaromatic ring may optionally and independently be further substituted by 1, 2 or 3 substituents selected from $CF_3$, methyl, iodo, bromo, fluoro and chloro;

$R^2$ is independently selected from ethyl and isopropyl;

$R^3$ is independently selected from hydrogen and fluoro;

$R^4$ is independently selected from —$NH_2$ and —$NHSO_2R^5$; and $R^5$ is independently selected from hydrogen, —$CF_3$ and $C_1$–$C_6$ alkyl, or salts thereof or separate enantiomers and salts thereof.

2. A compound according to claim 1, wherein $R^1$ is phenyl, pyrrolyl or furanyl; $R^2$ is ethyl or isopropyl; $R^3$ is hydrogen or fluoro; and $R^4$ is —$NH_2$, wherein said phenyl, pyrrolyl, and furanyl are optionally substituted with one or more groups selected from $CF_3$, methyl, iodo, bromo, fluoro, and chloro.

3. A method according to claim 1, wherein $R^1$ is phenyl, pyrrolyl, furanyl, thienyl or imidazolyl; $R^2$ is ethyl or isopropyl; $R^3$ is hydrogen or fluoro; $R^4$ is —$NH_2$ or —$NHSO_2R^5$; and $R^5$ is $C_1$–$C_6$ alkyl.

4. A method according to claim 1, wherein $R^1$ is phenyl, pyrrolyl, furanyl, thienyl or imidazolyl; $R^2$ is ethyl or isopropyl; $R^3$ is hydrogen; $R^4$ is —$NHSO_2R^5$; and $R^5$ is $C_1$–$C_6$ alkyl.

5. A method according to claim 1, wherein the $R^1$ heteroaromatic ring is substituted by 1, 2 or 3 substituents selected from $CF_3$, methyl, iodo, bromo, fluoro or chloro.

6. A method according to claim 1, wherein the $R^1$ heteroaromatic ring is substituted by 1, 2 or 3 substituents selected from methyl.

7. A method according to any one of claims 1–6, wherein the salt of the compound of formula I is a hydrochloride, dihydrochloride, sulfate, tartrate, ditrifluoroacetate, or citrate salt.

8. A method for treating anxiety, comprising administering to a subject suffering from anxiety a pharmaceutical composition comprising a compound of the formula I

III

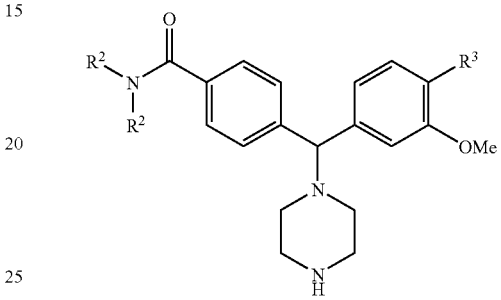

wherein $R^1$ is selected from any one of (i) phenyl

;

(ii) pyridinyl

;

(iii) thienyl

;

(iv) furanyl

;

(v) imidazolyl

;

(vi) triazolyl

;

-continued (vii) pyrrolyl

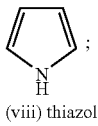

(viii) thiazolyl

(ix) pyridyl-N-oxide

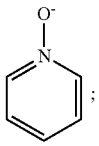

wherein each $R^1$ phenyl and $R^1$ heteroaromatic ring may optionally and independently be further substituted by 1, 2 or 3 substituents selected from $CF_3$, methyl, iodo, bromo, fluoro and chloro;

$R^2$ is independently selected from ethyl and isopropyl;
$R^3$ is independently selected from hydrogen and fluoro;
$R^4$ is independently selected from —$NH_2$ and —$NHSO_2R^5$; and
$R^5$ is independently selected from hydrogen, —$CF_3$ and $C_1$–$C_6$ alkyl, or salts thereof or separate enantiomers and salts thereof; and a pharmacologically and pharmaceutically acceptable carrier.

9. A method for treating anxiety, comprising administering to a subject suffering from anxiety an effective amount of at least one compound selected from:

4-[1-(4-Benzyl-piperazin-1-yl)-1-(4-fluoro-3-hydroxy-phenyl)-methyl]N,N-diisopropyl-benzamide;

4-[1-(4-Fluoro-3-hydroxy-phenyl)-1-(4-thiophen-3-ylm-ethyl-piperazin-1-yl)-methyl]-N,N-diisopropyl-benzamide;

4-{1-(4-Fluoro-3-hydroxy-phenyl)-1-[4-(1H-imidazol-2-ylmethyl)-piperazin-1-yl]-methyl}-N,N-diisopropyl-benzamide;

4-[1-(3-Amino-phenyl)-1-(4-benzyl-piperazin-1-yl)-methyl]-N,N-diisopropyl-benzamide;

4-[1-(3-Amino-phenyl)-1-(4-thiophen-3-ylmethyl-piperazin-1-yl)-methyl]-N,N-diisopropyl-benzamide;

4-{1-(3-Amino-phenyl)-1-[4-(1H-imidazol-2-ylmethyl)-piperazin-1-yl]-methyl}-N,N-diisopropyl-benzamide;

N,N-Diisopropyl-4-[1-(3-methanesulfonylamino-phenyl)-1-(4-thiophen-3-ylmethyl-piperazin-1-yl)-methyl]-benzamide;

4-([4-(3-furylmethyl)-1-piperazimyl]{3-[(methylsulfonyl)amino]phenyl}-N,N-diisopropyl-benzamide;

4-{(3-aminophenyl)[4-(3-thienylmethyl)-1-piperazinyl]methyl}-N,N-diethylbenzamide;

4-[(3-aminophenyl)(4-benzyl-1-piperazinyl)methyl]-N,N-diethylbenzamide; and 4-((4-benzyl-1-piperazinyl){3-[(methylsulfonyl)amino]phenyl}methyl)-N,N-diethylbenzamide.

* * * * *

UNITED STATES PATENT AND TRADEMARK OFFICE
CERTIFICATE OF CORRECTION

| | | |
|---|---|---|
| PATENT NO. | : 7,229,994 B2 | |
| APPLICATION NO. | : 10/477642 | |
| DATED | : June 12, 2007 | |
| INVENTOR(S) | : Brown et al. | |

It is certified that error appears in the above-identified patent and that said Letters Patent is hereby corrected as shown below:

In the claims:

At column 25, line 51, please replace "A compound according to claim 1" with --A method according to claim 1--

Signed and Sealed this

Sixth Day of May, 2008

JON W. DUDAS
*Director of the United States Patent and Trademark Office*